United States Patent [19]

Syrett et al.

[11] Patent Number: 4,658,365

[45] Date of Patent: Apr. 14, 1987

[54] DEVICE FOR IN-SITU MONITORING OF CORROSION RATE OF CATHODICALLY POLARIZED METALS

[75] Inventors: Barry C. Syrett, Palo Alto; Michael C. H. McKubre, Menlo Park, both of Calif.

[73] Assignee: Electric Power Research Institute, Inc., Palo Alto, Calif.

[21] Appl. No.: 576,119

[22] Filed: Feb. 2, 1984

[51] Int. Cl.$^4$ ............................................. G01N 27/46
[52] U.S. Cl. ................................... 364/496; 204/1 T; 204/147
[58] Field of Search ................................ 364/496, 555; 324/65 CR; 204/1 T, 400, 404, 410; 73/861.11, 861.12

[56] References Cited

U.S. PATENT DOCUMENTS

| | | | |
|---|---|---|---|
| 4,160,171 | 7/1979 | Merrick | 204/404 |
| 4,181,882 | 1/1980 | Isaacs et al. | 204/404 |
| 4,238,298 | 12/1980 | Tsuru et al. | 204/1 T |
| 4,351,703 | 9/1982 | Winslow, Jr. | 204/404 X |
| 4,425,193 | 1/1984 | Taylor | 204/1 T |

OTHER PUBLICATIONS

Bockris, Modern Electrochemistry, chapter 8, pp. 862–895.
Macdonald, Electrochemical Impedance Techniques in Corrosion Science, 1981, pp. 110–149.

Primary Examiner—Parshotam S. Lall
Assistant Examiner—Thomas G. Black
Attorney, Agent, or Firm—Flehr, Hohbach, Test, Albritton & Herbert

[57] ABSTRACT

A method of monitoring the rate of corrosion of a cathodically protected system, comprising superimposing a sinusoidal voltage on a cathodic protection voltage imposed on a portion of the system, measuring an anodic dissolution current in response to the superimposed voltage, and calculating the corrosion rate from the anodic dissolution current at the cathodic protection voltage potential.

3 Claims, 5 Drawing Figures (b) HIGH FREQUENCY MEASUREMENT CIRCUIT

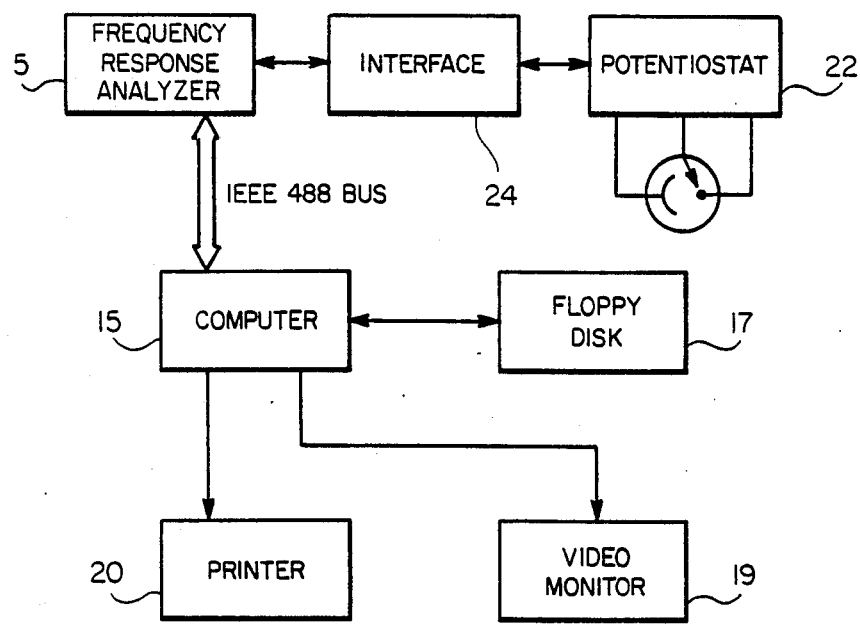
FIG_1
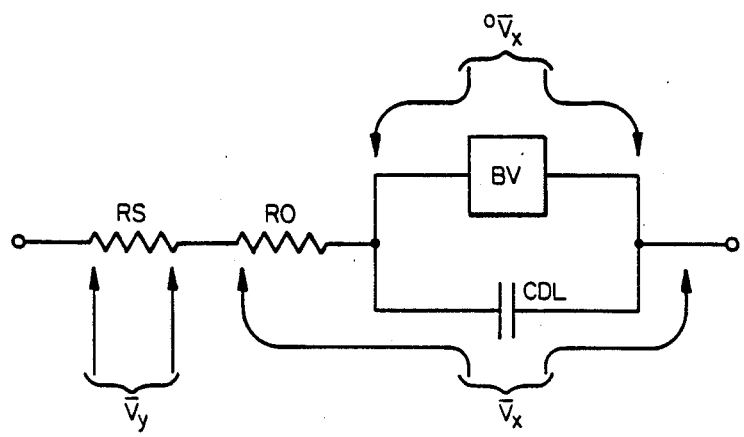
(b) HIGH FREQUENCY MEASUREMENT CIRCUIT
FIG_2

STRUCTURE OF HARMONIC DATA ARRAY ZN (16,50)
SAVED ON DISK AS HS-(NAME) AND HDM

| | | HS-ARRAY | HDM-ARRAY | |
|---|---|---|---|---|
| | | ZERO ELEMENT | FIRST ELEMENT | HIGHER ELEMENTS→ |
| 0 | MEASURED MODE | $f/Hz$ | $\omega\,rad.s^{-1}$ | INCREASING FREQUENCY→ |
| 1 | ARRAY WIDTH | $_1Z'$ | $_1^0V'_x$ | |
| 2 | ARRAY LENGTH | $_1Z''$ | $_1^0V''_x$ | |
| 3 | AC VOLTAGE | $_0V_x$ | | |
| 4 | INPUT RANGE | $_1V'_x$ | $_0Y$ | |
| 5 | DC VOLTAGE | $_1V''_x$ | | |
| 6 | SERIES RESISTANCE | $_0V_y$ | | |
| 7 | MAXIMUM HARMONIC | $_1V'_y$ | $_1Y'$ | |
| 8 | MINIMUM FREQUENCY | $_1V''_y$ | $_1Y''$ | |
| 9 | MAXIMUM FREQUENCY | $_2V'_y$ | $_2Y'$ | |
| 10 | NO. OF INTEGRATIONS | $_2V''_y$ | $_2Y''$ | |
| 11 | $_0V_x$ | $_3V'_y$ | $_3Y'$ | |
| 12 | $_0V_y$ | $_3V''_y$ | $_3Y''$ | |
| 13 | $_0^0V_x$ | $_4V'_y$ | $_4Y'$ | |
| 14 | NOT USED | $_4V''_y$ | $_4Y''$ | |
| 15 | NOT USED | $_5V'_y$ | $_5Y'$ | |
| 16 | NOT USED | $_5V''_y$ | $_5Y''$ | |

FIG_3

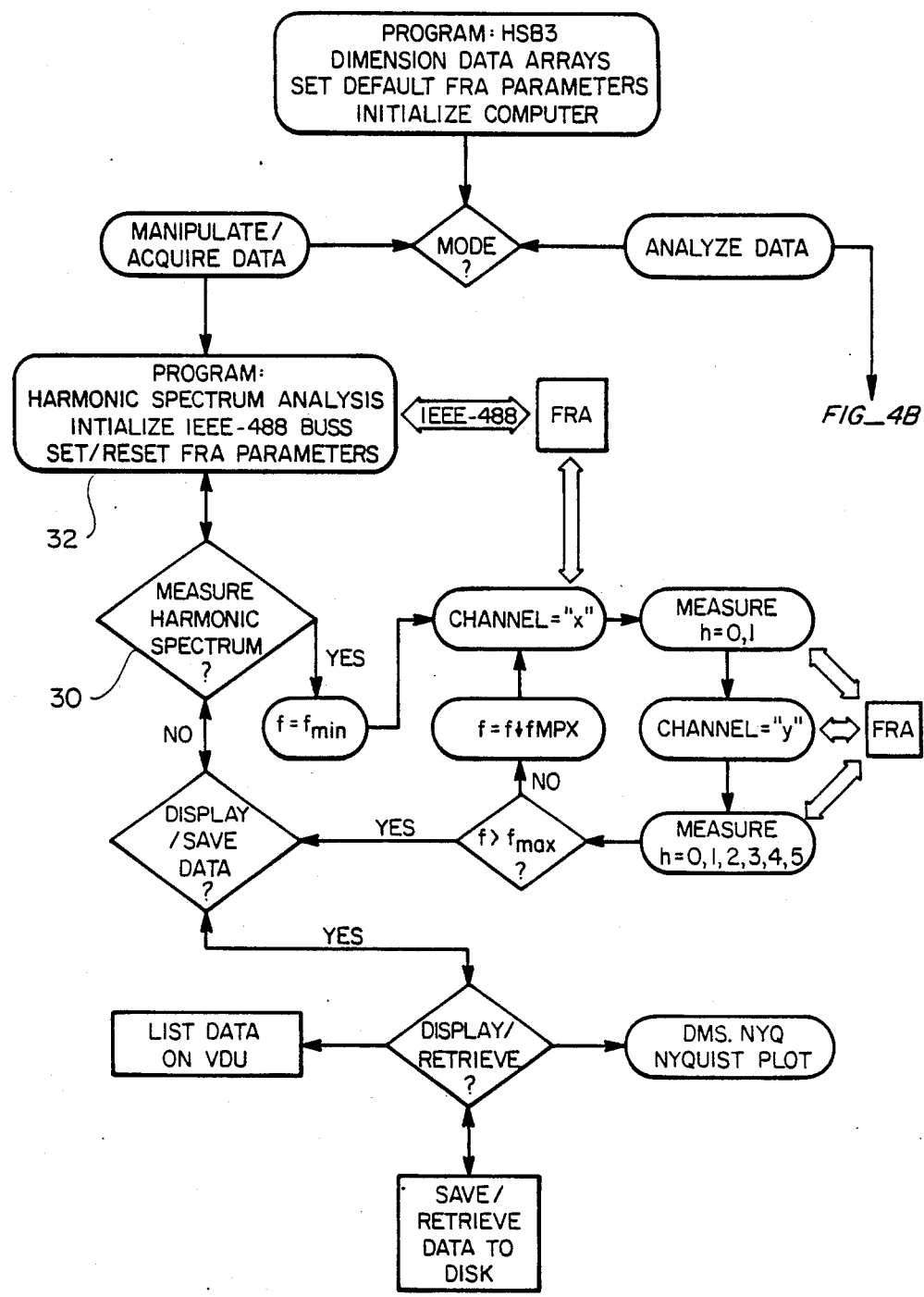
FIG_4A

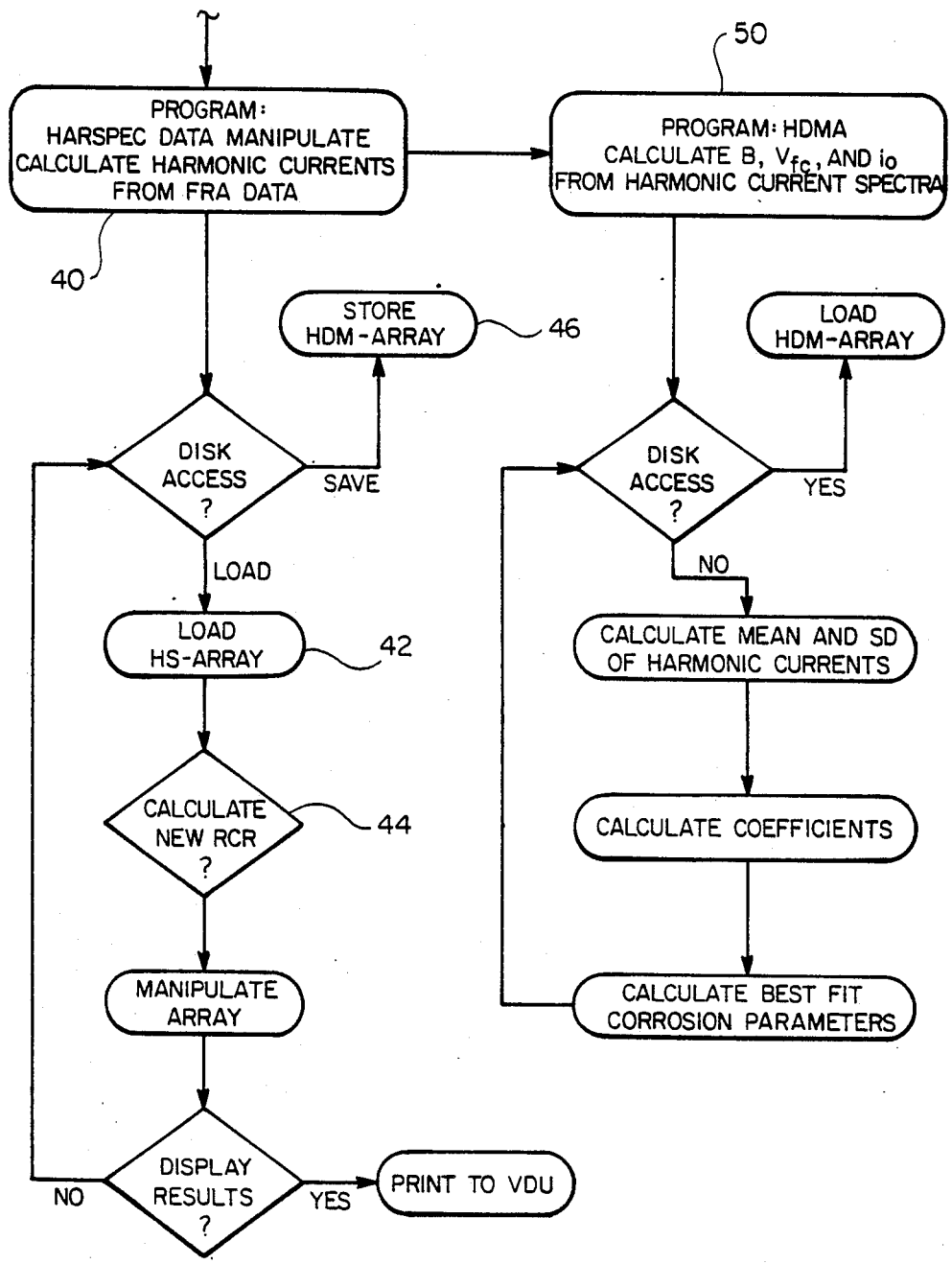
FIG_4B

DEVICE FOR IN-SITU MONITORING OF CORROSION RATE OF CATHODICALLY POLARIZED METALS

The subject invention is directed generally to methods of measuring corrosion rate in metals and to methods of protecting metals against corrosion, and more specifically to a method for measuring the instantaneous corrosion rate of a cathodically polarized metal.

An electrochemical technique known as the linear polarization method has been widely used for many years for measuring the instantaneous corrosion rate of freely corroding metals. In the linear polarization method, the polarization resistance ($R_p$) is measured in situ using a potentiostat and ancillary equipment. The $R_p$ value is related to the corrosion rate through a relationship developed by M. Stern and A. L. Geary and disclosed in the Journal of the Electrochemical Society Vol 104, page 56 (1957). This linear polarization (or polarization resistance $R_p$) method has gained widespread acceptability as a tool for monitoring the corrosion rate of freely corroding (unpolarized) metals in situ. But the equations developed by Stern and Geary, correlating in situ electrochemical measurements with corrosion rates are not valid when the metal is cathodically polarized (i.e. when the potential is shifted from the free corrosion potential to substantially more negative values by passage of an external current). Cathodic polarization of a metal usually reduces or effectively prevents corrosion of the metal and is the basis of the corrosion prevention technique known as cathodic protection.

Such cathodic protection systems are in wide use throughout industry. For instance, in the electric power industry, cathodic protection is used to prevent galvanic corrosion and inlet end erosion-corrosion, two forms of corrosion that occur in steam surface condensers. The susceptibility of metallic components to these forms of corrosion has been found to be minimized by installing a cathodic protection system in the water box. Such cathodic protection is achieved electrically by the use of counter electrodes and impressed current, or by galvanically coupling the condenser to more active (sacrificial) metals or alloys.

However, attempts to predict or measure the effect of cathodic protection on the corrosion rate of the tube as a function of distance from the inlet end are hampered by two technical problems. First, there is a distribution of potential and thus of corrosion rate within the tube. The form of the distribution depends in a complex way on the interfacial impedance (corrosion resistance), as well as on the tube and the electrolyte phase specific resistivity and the distance along the tube. Second, because the tube is held at a potential different from the corrosion potential, corrosion resistance measurements cannot be used in conjunction with the Stern-Geary relationship discussed above to provide an in situ determination of the corrosion rate. However, the problem of potential distribution is not severe for the essentially planar tubesheet; and the corrosion of this component is normally of the greater concern than the corrosion of the inlet end of the tubing.

A technique for monitoring such corrosion rates would be highly useful and have enormous potential for use, particularly when the environment has a varying corrosivity, for example in steam surface condensers where the coolant is occasionally, but not always polluted with sulfide.

It is therefore an object of the present invention to provide an electrochemical technique for monitoring the corrosion rate of a cathodically polarized structure.

The success or efficiency of a cathodic protection system is currently determined by making post test weight loss measurements on the cathodically protected metals. This is a time consuming process and the results are interpretable only if flow conditions and environmental conditions remain constant.

It is therefore an object of the present invention to provide an improved, automated method for determining corrosion rate in a cathodically protected device.

The above and other objectives of the present invention are achieved by a technique for electrochemical measurement of the anodic corrosion current ("corrosion rate") under conditions of an applied cathodic protection potential. The electrochemical parameters that are necessary to calculate the anodic corrosion rate are contained in the harmonic current response to a moderate amplitude sinusoidal voltage perturbation applied to the metallic component which is cathodically protected. The harmonic current response is analyzed at frequencies 1f, 2f, 3f, 4f, 5f and at the rectification current (the response of the DC current to the presence of the AC voltage, f=0) in response to a 20–50 mV AC voltage perturbation at a frequency f, superimposed on the DC cathodic protection voltage; the free corrosion current density, the free corrosion potential and the Tafel coefficients are calculated. The Tafel coefficient or Tafel slope is the measure of the intrinsic rate of corrosion in a material. From these data, the anodic dissolution current at the cathodic protection potential currently applied is calculated, which in turn is integrated with respect to time to yield a cumulative mass loss.

It is believed that the method disclosed herein can be a powerful research tool, allowing an investigator to rapidly evaluate the effects of changes in control potential or current, flow conditions, or water chemistry. Application of the results of this technique could further be used for monitoring the corrosion rate of any cathodically protected structure. Development of the method also would allow for provision of an interactive feedback system such that the cathodic protection current could always be maintained just sufficient to maintain a preselected, adequately low corrosion rate in the material of interest.

The invention can be best explained with reference to the following figure wherein:

FIG. 1 is a block diagram of the equipment used to develop the necessary parametric information to develop the data of interest:

FIG. 2 is an example of an equivalent circuit of the cathodically protected material under test showing the circuit components which must be solved to develop the anodic dissolution current.

FIG. 3 is a diagram showing the data which are developed and stored to provide a basis for calculation of the anodic dissolution current:

FIGS. 4A and 4B are block diagrams of the software which is used to acquire and analyze the data related to the system under test.

As discussed above this invention is directed to development of a means for measuring the corrosion rate as represented by the anodic component of the total current at the cathodic protection potential. This component can be represented by the following equation:

$$I_a = I_c \exp [A(V_{cp} - V_{fc})]$$

wherein the terms have the following meaning:
$I_c$ is the free corrosion current i.e. the corrosion rate in the absence of any corrosion protection.
A is the reciprocal of the anodic Tafel slope.
$V_{cp}$ is the cathodic protection potential.
$V_{fc}$ is the potential if there is no cathodic protection i.e. the open circuit or free corrosion potential.

The Tafel slope can best be explained by considering a specimen at the open circuit potential. If a current is passed to the specimen from a second electrode, as the current increases, the potential moves away from $V_{fc}$. By plotting the potential versus the logarithm of the current, a linear portion of the curve is revealed. This linear portion of the curve is the Tafel region, and the slope of this curve is the Tafel slope or Tafel coefficient. If the slope is positive, this is the anodic Tafel coefficient.

It is the corrosion current, $I_a$, which is related through Faraday's law to the mass loss of the cathodically protected material.

The constants which must be measured for the combination of metal and environment under test are shown in the first column of FIG. 3 and are measured using the equipment shown in FIG. 1. The frequency response analyzer 5 which is necessary to measure the harmonic current in response to the applied frequency is, for example, a Solartron model 1172/1183C/1185 frequency response analyzer, operated under microcomputer control 15. Data Storage is on a floppy disc 17; the results may also be displayed on a video monitor 19 or printed on a printer 20. The software developed for purposes of the control function and to allow regression of the data to the form desired, is included as appendices to this patent application. Measurements are made through a three electrode potentiostat 22, coupled to the frequency response analyzer 5 through an interface 24. Details of the interface can be found in SRI International final report to the U.S. Department of Energy entitled THE TEMPERATURE LIMITATION OF ALKALINE BATTERY ELECTRODES, by M. C. H. McKubre, 1981 published under D.O.E./L.B.L. subcontract 450561 and incorporated herein by reference.

The potentiostat 22 is itself a known device which is connected to three electrodes in the solution in which the metal under study is immersed. One electrode is the metal of interest also known as the working electrode; one is a reference electrode which has an electrochemical potential fixed with time; and one is a corrosion resistant counter-electrode that delivers current to the working electrode. The potentiostat measures the potential of the working electrode with respect to the reference electrode. If this potential is not equal to the desired (or "set") potential, the current passing between the counter and working electrodes is automatically adjusted so that the measured and set potentials are made equal.

The potentiostat can be used to change potentials for testing purposes. In this particular analysis, as will be seen from the software flow chart of FIG. 4, under control of the microcomputer 15, the frequency response analyzer 5 supplies a combined AC (at frequency f) and DC (cathodically protecting current) output to the potentiostat 22 via the signal conditioning interface 24. The potentiostat 22 closely maintains the set DC voltage between the working electrode or specimen and the reference electrodes, while the AC is supplied with attenuation and phase shift which increase with increasing frequency. The interface unit simultaneously provides the frequency response analyzer 5 with the voltage measured between the working and reference electrodes and the voltage across a resistor in series with the counter electrode, the latter being proportional to the current.

The harmonic components of the voltages supplied to the frequency response analyzer 5 are measured by a pulse rate multiplication technique. The frequency response analyzer 5 contains a two phase oscillator, operating at a multiple of the frequency supplied to the specimen. The frequency response analyzer 5 digitally computes the product of the unknown voltage and the in-phase quadrature oscillator output voltages with the internal oscillator set to the harmonic of interest. The integral (the equivalent of the sum in a discrete point digital device) of these products is computed over an integer number of cycles, normally N=1, 10, 100, 1000. This accomplishes a digitally demodulated phase-sensitive detection and results in numbers proportional to the magnitudes of the in-phase and quadrature components of the known voltage. The DC and fundamental components of the perturbing voltage (elements 3-5 of the array of FIG. 3), and the zero to 5th harmonics of the response function (FIG. 3, items 6-16) are measured sequentially as a function of frequency under control of microcomputer 15. The loop under which this is performed is the left hand side of the flow chart of FIG. 4 specifically the elements listed after the branch labeled yes following the decision to Measure Harmonic Spectrum 30. The controlling programs are listed in appendices A and B and labeled Harmonic Spectrum Boot which is the basic set up program for harmonic spectrum analysis 32, and Harmonic Spectrum. As shown in FIG. 4, meaurements are made at logarithmically spaced frequency points between a chosen minimum and maximum frequency. To minimize the transient effects, according to the software as incorporated, all harmonic measurements are made at each frequency before proceeding to the next. Communication over the IEEE standard 488 bus and the microcomputer 15 (for instance, a standard Apple II+ ® microcomputer) is bi-directional. The Apple II+ ® supplies AC and DC voltage, frequency, channel, harmonic number, and measurement initiate commands to the FRA 5. The FRA 5 returns real and imaginary components at the termination of measurement. The upper limit used in this preferred embodiment is 999.9 Hz as imposed by Solartron model 1185. To insure that the system is operating under kinetic control, and to employ long integration times with tests of relatively short duration, $f_{min}$ is normally set to 10 Hz. At the completion of the measurement cycle, the data is stored in memory in the computer 5 in the array shown in the column labeled HS-Array in FIG. 4. The validity of this data is assessed utilizing the software of appendix B by listing selected columns on the video monitor 19 and by plotting the complex ratio of the fundamental voltage and current on the display 19 using the program DMS.NYQ. If it is decided that the data are self-consistent, then the array can be given a designated name with a prefix HS to designate harmonic spectrum, and the data saved permanently on disc file 17 for subsequent analysis.

The substance under analysis and the associated analytical circuit can be represented by the equivalent circuit shown in FIG. 2. The element which according to accepted electrochemical theory controls the level of anodic corrosion current $I_a$ and therefore the corrosion rate is a component of element BV in FIG. 2. As can be seen this element is contained in an equivalent circuit comprising other ideal and non-ideal impedance elements.

That is, this invention is based on the assumption that an accurate measure of corrosion rate can be drawn from analysis of the harmonic current which arises from the fundamental voltage perturbation of the interfacial impedance element first identified by Butler and Volmer and discussed for example in "Electrochemical Impedance Techniques in Corrosion Science", authored by D. D. Macdonald and M. C. H. McKubre, in ASTM Special Technical Publication 727, Electrochemical Corrosion Testing, edited by F. Mansfeld and U. Bertocci, published by American Society for Testing and Materials, Philadelphia, P.A., 1981, pages 110–149, incorporated herein by reference. The measured harmonic currents which are in the data acquired using the data acquisition software shown on the left hand side of FIG. 4 must be analyzed to eliminate the influences of the uncompensated electrolyte resistance RO and the double layer capacitance CDL shown in FIG. 2. The data analysis is basically under the control of the routine labeled Harspec Data Manipulate and incorporated herein as appendix C. This subroutine 40 is first used to access the FRA data saved under the label HS. It is then used following step 42 to calculate values for the equivalent circuit and especially RO using the RCR regression software incorporated as appendix D and indicated at label 44. The results are stored as an HDM array as shown at step 46. From the data thus saved as HDM- (filename), the program HDMA 50 (which is a portion of appendix C) calculates the mean and standard deviation of the harmonic current component over the range of frequencies specified by the user. The values of the calculated harmonic current can be used to obtain the parameters of the corrosion equation. It has been found experimentally that maximum precision is available from the fundamental and second harmonic responses using the following equation:

$$\frac{2^I}{1^I} = \frac{X^2/4 + X^4/48 + X^6/1536}{X + X^3/8 + X^5/152}$$

The program HDMA step 50 solves iteratively for X and thus for B, the value of B can be substituted into the following equation to obtain $I_c$:

$$I_f = I_c[\exp(BV\sin[\omega t])\exp(B_oV_x)$$

$$-\exp(-AV\sin[\omega t])\exp(-A_oV_x)]$$

where $I_f$ is the Faradaic current in the external circuit. This leads to the development of the anodic current which in turn represents the anodic corrosion rate.

In summary, the disclosed method provides for the determination of corrosion rate in a cathodically protected system. The measurements may be performed in situ without disconnecting the cathodic protection system. To achieve the necessary speed and precision, harmonic measurements and data acquisitions are performed under control of microcomputer 15.

Other variations of the preferred embodiment disclosed herein may become apparent to one of skill in the art who studies the specification above. Therefore, the scope of the present invention is to be limited only by the appended claims.

What is claimed is:

1. A method of monitoring the rate of corrosion of a cathodically protected system, comprising superimposing a sinusoidal voltage on a cathodic protection voltage imposed on a portion of the system,
    measuring an anodic dissolution current in response to the superimposed voltage at each of a plurality of harmonics of said anodic dissolution current, including measuring a rectification current which comprises the DC response of the anodic dissolution current to the presence of said superimposed sinusoidal voltage; and
    calculating the corrosion rate from the anodic dissolution current at the cathodic protection voltage potential.

2. A method as claimed in claim 1 wherein said sinusoidal voltage is at frequency f, said response being measured at regular harmonics h of the response frequencies.

3. A method as claimed in claim 2 wherein the harmonic current response is measured at n·h for n=0,1,2,3,4,5.

* * * * *